United States Patent [19]

Giersch et al.

[11] Patent Number: 4,990,495
[45] Date of Patent: Feb. 5, 1991

[54] OXYGEN CONTAINING MACROCYCLIC COMPOUNDS, A PROCESS FOR THEIR PREPARATION AND THEIR USE AS PERFUMING INGREDIENTS

[75] Inventors: Wolfgang K. Giersch, Bernex; Karl-Heinrich Schulte-Elte, Onex, both of Switzerland

[73] Assignee: Firmenich S.A., Geneva, Switzerland

[21] Appl. No.: 436,403

[22] Filed: Nov. 14, 1989

[30] Foreign Application Priority Data

Dec. 23, 1988 [CH] Switzerland ............ 4791/88

[51] Int. Cl.$^5$ ............................................. A61K 7/46
[52] U.S. Cl. ................................. 512/8; 252/174.11; 512/12
[58] Field of Search ............... 512/8, 12; 568/375, 568/667; 549/434; 252/174.11

[56] References Cited

U.S. PATENT DOCUMENTS

| | | | |
|---|---|---|---|
| 2,529,825 | 11/1950 | Stoll .................................. | 568/375 |
| 3,128,304 | 4/1964 | Lafont ............................... | 512/8 |
| 3,227,742 | 1/1966 | Lafont et al. ..................... | 549/435 |
| 3,801,600 | 4/1974 | Naegeli et al. ................... | 512/12 |
| 4,183,965 | 1/1980 | Mookherjee et al. ............ | 568/375 |
| 4,241,225 | 12/1980 | Galdwin ........................... | 568/652 |
| 4,268,443 | 5/1981 | Bruns et al. ...................... | 512/12 |
| 4,460,498 | 7/1984 | Giersch et al. ................... | 512/8 |

FOREIGN PATENT DOCUMENTS

| | | | |
|---|---|---|---|
| 3300340 | 7/1984 | Fed. Rep. of Germany ...... | 568/375 |
| 61-134336 | 6/1986 | Japan ................................. | 568/667 |

Primary Examiner—James H. Reamer
Attorney, Agent, or Firm—Pennie & Edmonds

[57] ABSTRACT

Oxygen containing macrocyclic compounds of formula

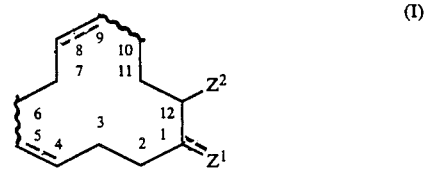

wherein
(a) the dotted lines indicate the location of an endocyclic single or double bond in positions 4 and 8 of the ring and of an exocyclic carbon-oxygen single bond in position 1, the wavy lines define a C—C bond of E or Z configuration when the bond in positions 4 and 8 is a double bond, and the symbols $Z^1$ and $Z^2$, taken together, define a cyclic acetal or ketal group represented by the formula

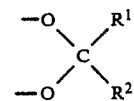

wherein the symbols $R^1$ and $R^2$, identical or different, represent each an alkyl radical, linear or branched, containing from 1 to 6 carbon atoms, or one of said symbols represents a hydrogen atom and the other an alkyl radical defined as above;
or wherein
(b) the symbol $Z^1$ stands for an oxygen atom or an OH group, the dotted lines indicate the location of an endocyclic single or double bond in positions 4 and 8 of the ring and of an exocyclic carbon-oxygen single ($Z^1$=OH) or double ($Z^1$=O) bond in position 1, the wavy lines define a C—C bond of E or Z configuration when the bond in positions 4 and 8 is a double bond, and the symbol $Z^2$ stands for a group $OR^3$, wherein $R^3$ represents a linear or branched alkyl radical, containing from 1 to 6 carbon atoms, are novel compounds which have useful odor properties. They can be used as active ingredients in perfuming compositions are perfumed products, to which they confer spicy-aldehydic type odor notes.

A process for the preparation of the compounds of formula (I) is also disclosed.

4 Claims, No Drawings

OXYGEN CONTAINING MACROCYCLIC COMPOUNDS, A PROCESS FOR THEIR PREPARATION AND THEIR USE AS PERFUMING INGREDIENTS

BRIEF SUMMARY OF THE INVENTION

The present invention relates to the fragrance industry. More particularly, it concerns a method to confer, enhance, improve or modify the odor properties of a perfuming composition or perfumed product, which method comprises adding to said composition or product a fragrance effective amount of a compound of formula

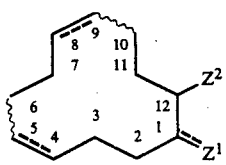
(I)

wherein
(a) the dotted lines indicate the location of an endocyclic single or double bond in positions 4 and 8 of the ring and of an exocyclic carbon-oxygen single bond in position 1, the wavy lines define a C—C bond of E or Z configuration when the bond in positions 4 and 8 is a double bond, and the symbols $Z^1$ and $Z^2$, taken together, define a cyclic acetal or ketal group represented by the formula

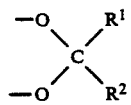

wherein the symbols $R^1$ and $R^2$, identical or different, represent each an alkyl radical, linear or branched, containing from 1 to 6 carbon atoms, or one of said symbols represents a hydrogen atom and the other an alkyl radical defined as above; or wherein (b) the symbol $Z^1$ stands for an oxygen atom or an OH group, the dotted lines indicate the location of an endocyclic single or double bond in positions 4 and 8 of the ring and of an exocyclic carbon-oxygen single ($Z^1$=OH) or double ($Z^1$=O) bond in position 1, the wavy lines define a C—C bond of E or Z configuration when the bond in positions 4 and 8 is a double bond, and the symbol $Z^2$ stands for a group $OR^3$, wherein $R^3$ represents a linear or branched alkyl radical, containing from 1 to 6 carbon atoms.

The invention also provides a perfuming composition or a perfumed product comprising as a perfuming ingredient a compound of formula (I) defined as above.

A further object of the present invention is a process for the preparation of the compounds of formula (I), which process comprises the following subsequent steps:

a. the reaction, in the presence of an acidic agent, of a diol of formula

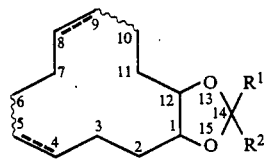
(II)

wherein the dotted lines indicate the location of a single or double bond in positions 5 and 9 of the ring, and the wavy lines define a C—C bond of E or Z configuration when the bond in positions 5 and 9 is a double bond, with a compound of formula

wherein $R^1$ and $R^2$ are defined as in claim 1, to obtain a ketal of formula

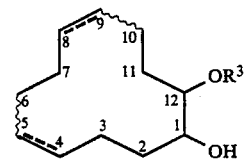
(III)

wherein the wavy lines and the symbols $R^1$ and $R^2$ are defined as above, and the dotted lines indicate the location of a single or double bond in positions 4 and 8 of the ring;

b. the reaction of the ketal of formula (III) with a reducing agent to obtain an hydroxy-ether of formula

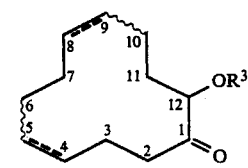
(IV)

wherein the dotted lines indicate the location of a single or double bond in positions 4 and 8 of the ring, the wavy lines define a C—C bond of E or Z configuration when the bond in positions 4 and 8 is a double bond, and the symbol $R^3$ is defined as in claim 1;

c. the reaction of the hydroxy-ether of formula (IV) with an oxidising agent to obtain a keto-ether of formula (V)

wherein the dotted lines, the wavy lines and the symbol $R^3$ are defined as in b.

A still further object of the present invention is to provide a novel compound of formula (I) defined as above with the proviso that when $Z^1$ is oxygen, $Z^2$ cannot be a methyl radical.

BACKGROUND OF THE INVENTION

Amongst the compounds represented by general formula (I) defined as above, 2-methoxycyclododecanone and 12-methoxy-4,8-cyclododecadien-1-one, are known chemical entities [see, for instance, L. Chow-Yan et al., Can. J. Chem. 57, 2923 (1979) and B. Foehlisch et al., Tetrahedron Lett. 21, 3005 (1980)]. However, we could find no mention in the prior art references that might indicate that these compounds possessed useful odor properties.

THE INVENTION

We have now discovered that both the cited prior art compounds and the novel compounds of formula (I) possess very interesting odor properties and that, as a result, they can be used as active fragrance ingredients to perfume a variety of articles such as soaps, cosmetic preparations, shampoos, detergents, fabric softeners or household products, as well as for the preparation of perfuming bases and concentrates.

In particular, one can cite, as preferred compounds according to the invention, the keto-ether derivatives of 4,8-cyclododecadiene, i.e. the compounds of formula (I) wherein the symbol $Z^1$ represents an oxygen atom, the dotted lines indicate the location of an endocyclic double bond in positions 4 and 8 of the ring and of an exocyclic carbon-oxygen double bond in position 1, the wavy lines define a C—C bond of E or Z configuration, and the symbol $Z^2$ stands for an $OR^3$ group, wherein $R^3$ is an alkyl radical, linear or branched, containing from 1 to 6 carbon atoms. These compounds show in effect quite unexpected odor properties since, unlike what could be expected from prior art studies on other cyclododecane derivatives [see, for instance, H. Aebi et al. in Kosmetika, Riechstoffe und Lebensmittelzusatzstoffe, ed. Georg Thieme Verlag, Stuttgart (1978)] and in spite of their keto-ether structure, these compounds develop aldehydic notes.

Amongst these keto-ether derivatives, 12-pentyloxy-4,8-cyclododecadien-1-one is cited here as a more preferred compound according to the invention. This compound is particularly interesting as it develops a fruity-calamus odor, aromatic in the direction of coriander, with a strong aldehydic note. Furthermore, its odor note has a spicy tonality in the direction of cascarilla. The combination of these two sides of the odor note, on the one hand, fruity-calamus and, on the other hand, spicy-cascarilla, is quite unique for a synthetic compound and its keto-ether structure implies that this compound is more stable than the aldehydes in general. As a result of the varied facets of its odor note, this compound can find wide use in a variety of applications and it is particularly convenient for the preparation of perfuming compositions of various types, to which it confers more volume and power, in addition to imparting to the composition its specific odor characters. The use of this compound in masculine colognes is particularly successful. On the other hand, this compound can be added to a variety of perfumed articles and namely to powder detergents, wherein it enhances the volume of their fragrance.

Other preferred compounds according to the invention are 12-(2,2-dimethylpropoxy)-4,8-cyclododecadien-1-one and 12-isobutoxy-4,8-cyclododecadien-1-one which can be used in the same type of applications as those mentioned above.

As previously cited, the compounds of the invention and, namely, the keto-ether derivatives of cyclododecane and cyclododecadiene can be used as active fragrance ingredients in perfuming compositions, bases and concentrates, and likewise for the preparation of perfumed products such as soaps, detergents, fabric softeners, household products and cosmetic preparations.

The proportions in which these compounds can be used to achieve a perfuming effect, namely in perfuming compositions, can vary between 5 and 10% in weight, relative to the weight of composition. However, these values are cited here merely for the sake of example, since the man in the art knows by experience that such proportions can vary in a wide range of values, as a function of the other coingredients in the particular perfuming base to which the compounds of the invention are added and of the fragrance effect desired.

The instant invention also provides a process for the preparation of the compounds of formula (I), starting from either 1,2-cyclododecadienol or 5,9-cyclododecadiene-1,2-diol, both represented by the general formula

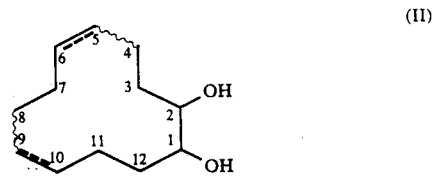

(II)

wherein the dotted lines indicate the location of a single or double bond in positions 5 and 9 of the ring and the wavy lines define a C—C bond of E or Z configuration when the bond in position 5 and 9 is a double bond. The reaction of diols (II) with a compound of formula

wherein symbols $R^1$ and $R^2$ are defined as in claim 1. gives ketals of formula

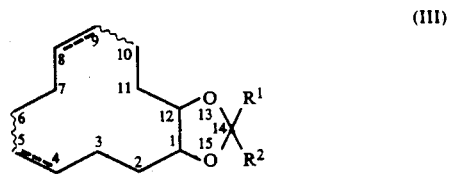

(III)

wherein the wavy lines and the symbols $R^1$ and $R^2$ are defined above and the dotted lines indicate the location of a single or double bond in positions 4 and 8 of the ring.

According to the invention, this reaction is carried out in the presence of an acidic agent which can be a protonic mineral or organic acid, or yet a Lewis type acid. Moreover, the reaction takes place in the presence of an organic solvent such as petroleum ether.

The diols of formula (I), used as starting materials in the process according to the invention, can be obtained either commercially, or following known preparation processes [see M. Ohno et al., Bull, Chem. Soc. Japan 39, 316 (1966), L. I. Zakharkin et al., Dokl. Akad. Nauk. SSSR 132, 1078 (1960) and V. Kosswig, Chem. Zeitg. 96, 373 (1972)].

As directly obtained from this reaction, the compounds of formula (III) wherein the dotted lines stand for double bonds, present themselves in the form of mixtures of three isomeric forms resulting from the E or Z configuration isomerism of the two C—C bonds in positions 5 and 9 of the ring. For practical and economical reasons, these mixtures of isomers obtained directly from the above-described reaction will be used preferentially as starting products in the synthesis of the compounds of formula (IV) described hereinafter.

According to the invention, the reaction of ketals (III) with a reducing agent provides the hydroxy-ethers of formula

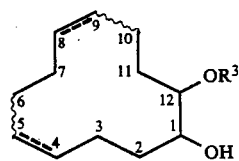

(IV)

wherein the dotted lines indicate the location of a single or double bond in positions 4 and 8 of the ring, the wavy lines designate a C—C bond of E or Z configuration when the bond in positions 5 and 8 is a double bond, and the symbol $R^3$ is defined as in claim 1.

The reduction of the ketal derivative is carried out under known conditions, by means of, for example, LiAlH$_4$/AlCl$_3$ [see E. L. Eliel et al., J. Amer. Chem. Soc. 84, 2371 (1962)] or of DIBAH (diisobutylaluminum hydride) [see K. Ishikara et al., Tetrahedron Lett. 1987, 6613].

The cyclododecane hydroxy-ether derivatives of formula (IV) directly issued from the preceding reaction are mixtures of two isomeric forms corresponding to the E or Z configuration of the C—O exocyclic bonds in positions 1 and 12 of the ring. When the compounds of formula (IV) are hydroxy-ether derivatives of 4,8-cyclododecadiene, they may take several isomeric forms, resulting from the combined E/Z isomerism of the C—O exocyclic bonds with that of the C—C bonds previously cited. Yet again, the mixtures of isomers directly issued from the reaction will be preferentially used in the perfumery applications, as well as starting products in the synthesis of the keto-ethers of formula (V) described hereafter.

According to the process of the invention, the keto-ethers of formula

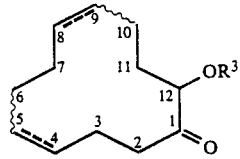

(V)

wherein the dotted lines stand for a single or double bond in positions 4 and 8 of the ring, the wavy lines represent a C—C bond of E or Z configuration when the bond in positions 4 and 8 is a double bond, and the symbol $R^3$ defines an alkyl radical, linear or branched, containing from 1 to 6 carbon atoms, are prepared by reaction of the hydroxy-ethers (IV) with an oxidising agent. The oxidation reaction of the hydroxy-ether is carried out under known conditions, using as oxidising agent, for example, PDC (pyridinium dichromate) [see E. J. Corey et al., Tetrahedron Lett. 1979, 399] or PCC (pyridinium chlorochromate) [see E. J. Corey et al., Tetrahedron Lett. 1975, 2647].

The keto-ethers of formula (V) wherein the dotted lines designate a double bond can take three isomeric forms resulting from the combination of E/Z configurations of the C—C bonds adjacent to the said double bonds. The products directly issued from the synthesis are in fact mixtures of these isomers and, for the reasons already cited, they are preferentially used as perfuming ingredients according to the invention.

The Tables I to III, presented hereinafter, list the compounds prepared according to the process of the invention, as well as their boiling points and the yield of their respective synthesis. Table I also lists, facing each of the compounds obtained, the respective aldehyde or ketone used as a starting product in the corresponding synthesis.

The invention will now be described in a more detailed manner by way of the following examples related to preferred compounds according to the invention. The latter must not, however, be construed as being limited to the embodiments thus illustrated.

TABLE I

Ketals of general formula (III)

| Compound | Starting product of formula $R^1\!\!\!\diagdown\!\!\!\!_{R^2}\!\!\!\diagup\!\!=\!O$ | Boiling point (bulb-to-bulb distillation) °C./Pa | Yield % |
|---|---|---|---|
| 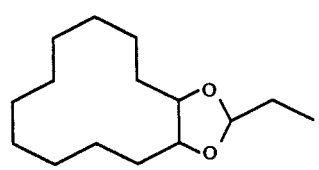 | 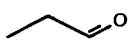 | 120/4.0 | 63 |

TABLE I-continued
Ketals of general formula (III)
| Compound | Starting product of formula $\overset{R^1}{\underset{R^2}{>}}=O$ | Boiling point (bulb-to-bulb distillation) °C./Pa | Yield % |
|---|---|---|---|
|  | 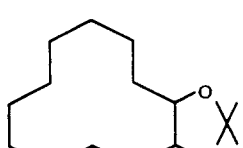 | 100/3.3 | 89 |
| 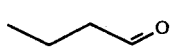 | 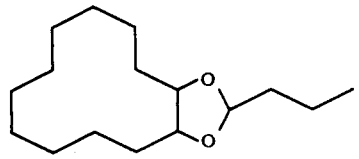 | 120/4.0 | 95 |
|  | 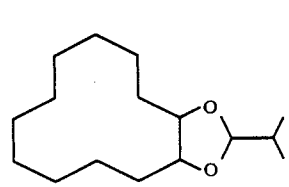 | 130/5.4 | 90 |
|  | 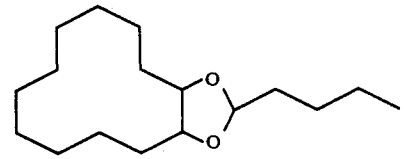 | 125/4.4 | 92 |
|  | 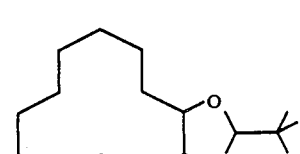 | 115/6.0 | 76 |
|  | 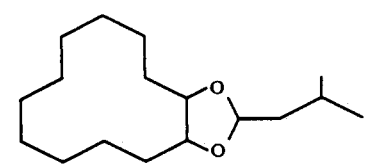 | 120/4.0 | 93 |
| 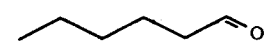 | 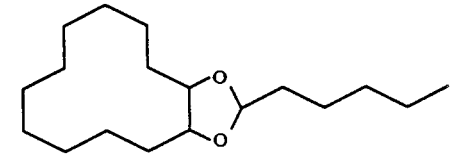 | 125/4.0 | 92 |
| 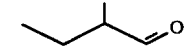 | 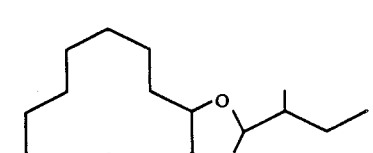 | 105/3.7 | 32 |

TABLE I-continued

Ketals of general formula (III)

| Compound | Starting product of formula $\begin{array}{c}R^1\\ \phantom{R}\rangle=O\\ R^2\end{array}$ | Boiling point (bulb-to-bulb distillation) °C./Pa | Yield % |
|---|---|---|---|
| [macrocyclic dioxolane with n-propyl] | butanal | 135/5.4 | 80 |
| [macrocyclic dioxolane with isopropyl] | isobutanal | 100/4.0 | 93 |
| [macrocyclic dioxolane with isobutyl] | 3-methylbutanal | 120/3.7 | 92 |
| [macrocyclic dioxolane with tert-butyl] | pivaldehyde | 115/6.0 | 78 |
| [macrocyclic dioxolane with n-butyl] | pentanal | 130/6.0 | 90 |
| [macrocyclic dioxolane with sec-butyl] | 2-methylbutanal | 100/4.0 | 93 |
| [macrocyclic dioxolane with isopropyl, methyl] | 3-methyl-2-butanone | 105/6.1 | 42 |
| [macrocyclic dioxolane with gem-dimethyl] | acetone | 95/3.1 | 93 |

TABLE I-continued

Ketals of general formula (III)

| Compound | Starting product of formula $\begin{matrix}R^1\\R^2\end{matrix}=O$ | Boiling point (bulb-to-bulb distillation) °C./Pa | Yield % |
|---|---|---|---|
| 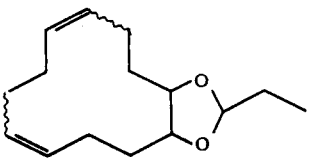 |  | 95/4.0 | 73 |

TABLE II

Compounds of general formula (IV)

  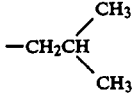

| R³ | Boiling point (bulb-to-bulb distillation) °C./pa | Yield % | Boiling point (bulb-to-bulb distillation) °C./Pa | Yield % |
|---|---|---|---|---|
| —CH₂CH₂CH₃ | 130/5.0 | 82 | 130/5.4 | 81 |
| —CH(CH₃)₂ 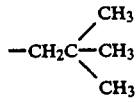 | 120/5.2 | 90 | 110/3.5 | 89 |
| —CH₂CH₂CH₂CH₃ | 130/3.5 | 89 | 125/3.7 | 88 |
| —CH₂CH(CH₃)₂ | 110/3.7 | 85 | 100/4.6 | 79 |
| —CH₂CH₂CH₂CH₂CH₃ | 150/4.2 | 93 | 120/7.2 | 88 |
| —CH₂C(CH₃)₃ | 130/4.0 | 83 | 115/4.0 | 92 |
| —CH₂CH₂CH(CH₃)₂ | 120/4.2 | 81 | 120/3.9 | 86 |
| —CH₂CH₂CH₂CH₂CH₂CH₃ | 150/4.2 | 97 | — | — |
| —CH₂CH(CH₃)CH₂CH₃ | 110/3.0 | 78 | 110/4.0 | 72 |
| (CH₃)₂CHCH(CH₃) 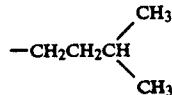 | — | — | 145/6.8 | 73 |

TABLE III

Compounds of general formula (V)

| R³ | Boiling point (bulb-to-bulb distillation) °C./Pa | Yield % | Boiling point (bulb-to-bulb distillation) °C./Pa | Yield % |
|---|---|---|---|---|
| —CH₂CH₂CH₃ | 95/9.0 | 83 | 105/3.8 | 81 |
| —CH(CH₃)₂ | 115/5.6 | 86 | 95/5.2 | 77 |
| —CH₂CH₂CH₂CH₃ | 115/4.2 | 83 | 95/5.4 | 51 |
| —CH₂CH(CH₃)₂ | 100/4.6 | 69 | 105/5.4 | 73 |
| —CH₂CH₂CH₂CH₂CH₃ | 130/4.0 | 26 | 120/7.2 | 75 |
| —CH₂C(CH₃)₃ | 95/3.5 | 89 | 95/4.0 | 86 |
| —CH₂CH₂CH(CH₃)₂ | 95/3.5 | 68 | 100/4.6 | 73 |
| —CH₂CH₂CH₂CH₂CH₂CH₃ | 160/7.2 | 45 | — | — |
| —CH₂CH(CH₃)(CH₂CH₃) | 115/4.8 | 68 | 105/4.2 | 60 |
| (H₃C)₂CHCH(CH₃)— | — | — | 140/5.8 | 81 |

EXAMPLE 1

(a) 5 g of 5,9-cyclododecadien-1,2-diol, 2.4 g of valeric aldehyde, a spatula of p-toluenesulfonic acid and 200 ml of 80/100 petroleum ether were charged into a 250 ml two-neck flask equipped with a water separator and the mixture was taken to reflux for 1 h. The reaction mixture was then poured on ice, neutralized with brine, dried and concentrated. Distillation in a bulb-to-bulb apparatus produced 6.06 g of 14-butyl-13,15-dioxabicyclo[10.3.0]pentadeca-4,8-diene.

B.p. 130° C./6.0 Pa; yield 90%.
IR: no function.
NMR (60 Mz): 0.9(tr,J=6 Hz,3H); 3.6–4.4(m,2H); 4.8–5.15(m,1H); 5.3–5.7(m,4H) δ ppm.
GC-MS: (2 peaks, approx. 1:1): (1) 264(M+,3),207(21),161(83), 133(27), 119(38), 91(48), 79(91), 67(100), 41(81). (2) 264(M+, less than 1), 207(31), 161(100), 133(29), 119(41), 91(48), 79(92), 67(88), 41(66).

(b) 38.2 ml of a 1.2M solution of DIBAH in toluene were charged into a 100 ml three-neck flask and a toluene solution of the ketal prepared as in (a), obtained from 6.15 g of 14-butyl-13,15-dioxabicyclo[10.3.0]pentadeca-4,8-diene and 20 ml of toluene, was added dropwise. After refluxing for 1 h, the reaction mixture was then poured on ice and acidified to dissolve the aluminum salts and, afterwards, neutralized, dried and concentrated. Distillation in a bulb-to-bulb apparatus provided 5.76 g of 12-pentyloxy-4,8-cyclododecadien-1-ol.

B.p. 130° C./4.2 Pa; yield 93%.
IR: 3430 cm⁻¹.
NMR (60 MHz): 0.91(tr,J=6 Hz,3H); 2.4(OH); 3.42(m,2H); 3.8(m,2H); 5.2–5.7(m,4H) δ ppm.
GC-MS (1 large peak): 266(M+,19), 196(3), 178(6), 133(7), 97(16), 81(36), 67(28), 55(30), 43(100).

(c) 8.8 g of diatomaceous earth and a solution of 5.39 g of 12-pentyloxy-4,8-dodecadien-1-ol in 50 ml of dichloromethane were charged into a 250 ml flask. 8.8 g of PCC were then added in small portions and the mixture was stirred for 2 h at room temperature. Ethyl ether was added to the reaction mixture to precipitate the chromium salts, and the mixture was then filtered on SiO$_2$, concentrated and distilled in a bulb-to-bulb apparatus. 4 g of 12-pentyloxy-4,8-cyclododecadien-1-one were obtained.

B.p. 120° C./7.2 Pa; yield 75%.

IR: 1715 cm$^{-1}$.

NMR (60 Mz): 0.91(tr,J=6 Hz,3H); 3.25-3.85(m,3H); 5.0-5.7(m,4H) δ ppm.

GC-MS (2 peaks, approx. 1:1): (1) 264 (M+,0), 196(2), 176(1), 160(3), 133(5), 119(11), 107(8), 94(12), 79(28), 67(33), 55(31), 43(100). (2) 264 (M+,0), 196(2), 133(5), 119(8), 97(13), 79(33), 67(32), 55(31), 43(100).

Odor properties: spicy-aldehydic, light metallic note, powerful.

EXAMPLE 2

(a) 5 g of 5,9-cyclododecadien-1,2-diol, 2.4 g of pivalic aldehyde, 1 spatula of p-toluenesulfonic acid and 100 ml of 80/100 petroleum ether were charged into a 250 ml two-neck flask equipped with a water separator and the mixture was taken to reflux for 2 h. The reaction mixture was subsequently boured on ice, washed to neutrality with brine, dried and concentrated. After distillation in a bulb-to-bulb apparatus, 5.2 g of 14-tert-butyl-13,15dioxabicyclo[10.3.0]pentadeca-4,8-diene were obtained.

B.p. 115° C./6.0 Pa; yield 78%.

IR: no function.

NMR (60 MHz): 0.9 and 0.92(2s,9H); 3.7-4.4(m,2H); 4.5 and 4.62(2s,1H), 5.3-5.7(m,4H) δ ppm.

GC-MS (2 peaks, approx. 1:2): (1) 264 (M+,0), 263(1), 207(57), 161(100), 133(27), 119(26), 91(37), 79(48), 67(50), 41(78). (2) 264 (M+,1), 207(57), 161(100), 133(28), 119(29), 91(31), 79(50), 67(49), 41(73).

(b) Preparation steps identical to those described in example 1(b) were carried out using 5.2 g of 14-tert-butyl-13,15-dioxabicyclo[10.3.0]pentadeca-4,8-diene and 32.8 ml of a 1.2M solution of DIBAH in toluene. After acidification, the reaction mixture was washed with ether, then with brine, dried, concentrated and distilled in a bulb-to-bulb apparatus. 4.82 g of 12-(2,2-dimethylpropoxy)-4,8-cyclododecadien-1-ol were obtained.

B.p. 115° C./4.0 Pa; yield 92%.

IR: 3420 cm$^{-1}$.

NMR (60 MHz): 0.91(s,9H); 3.12(s,2H); 3.4(m,1H); 3.85(m,1H); 5.3-5.6(m,4H) δ ppm.

GC-MS (2 peaks, approx. 9:1): (1) 266 (M+,1), 196(9), 133(8), 109(7), 93(13), 81(32), 71(85), 43(100). (2) 266 (M+,0), 252(4), 196(2), 178(3), 133(10), 119(12), 109(14), 97(31), 81(80), 67(66), 57(78), 41(100).

(c) The method employed was identical to that described in example 1(c), but using as starting products 4.82 g of 12-(2,2-dimethylpropoxy)-4,8-dodecadien-1-ol, 7.8 g of PCC and 50 ml of dichloromethane. The stirring was carried out for 1 h. 4.11 g of 12-(2,2-dimethylpropoxy)-4,8-cyclododecadien-1-one were obtained.

B.p. 95° C./4.0 Pa; yield 86%.

IR: 1710 cm$^{-1}$.

NMR (60 MHz): 0.92 and 0.96(2s, approx. 2:1,9H); 3.02(s,2H); 3.7(m,1H); 5.2-5.6(m,4H) δ ppm.

GC-MS (2 peaks, approx. 2:1): (1) 264 (M+,15), 207(1), 196(7), 176(3), 148(4), 133(4), 120(5), 109(4), 93(7), 79(10), 71(81), 43(100). (2) 264 (M+,17), 207(2), 196(7), 176(3), 166(5), 149(3), 133(3), 119(5), 97(9), 79(9), 71(88), 43(100).

Odor properties: spicy-marine-green, natural calamus-cardamom odor.

EXAMPLE 3

(a) Procedure identical to that described in example 1(a) but using 5 g of 5,9-cyclododecadien-1,2-diol, 20.2 g of isobutyric aldehyde and 100 ml of 80/100 petroleum ether. 5.92 g of 14-isopropyl-13,15-dioxybicyclo[10.3.0]pentadeca-4,8-diene were obtained.

B.p. 100° C./4 Pa; yield 93%.

IR: no function.

NMR (60 MHz): 0.93(d,J=7 Hz, 6H); 3.7-4.4(m,2H); 4.6 and 4.76(2d, J approx.=5 Hz,1H); 5.3-5.7(m,4H) δ ppm.

GC-MS (1 large peak): 250(M+,2), 107(52), 161(100), 133(27), 119(32), 91(36), 79(56), 67(52), 41(73).

(b) The same procedure as that described in example 2(b) was followed but using 5.92 g of 14-isopropyl-13,15-dioxabicyclo[10.3.0]pentadeca-4,8-diene and 39.5 ml of a 1.2M solution of DIBAH in toluene. 4.71 g of 12-isobutoxy-4,8-cyclododecadien-1-ol were obtained.

B.p. 100° C./4.6 Pa; yield 79%.

IR: 3450 cm$^{-1}$.

NMR (60 MHz): 0.92(d,J=7 Hz,6H); 2.2(OH); 3.32(d,J=7 Hz,2H); 3.2-4.2(m,2H); 5.2-5.6(m,4H) δ ppm.

GC-MS (1 peak): 252 (M+,12), 196(12), 178(7), 133(9), 109(9), 81(29), 67(31), 57(75), 41(100).

(c) 4.71 g of 12-isobutoxy-4,8-cyclododecadien-1-ol were dissolved in 50 ml of dichloromethane and 8 g of diatomaceous earth were added to this solution, in suspension. After stirring, 8.05 g of PCC were added in small portions, the reaction mixture having been kept under stirring, at room temperature, for 2 h. Afterwards, the chromium salts were precipitated with ethyl ether and the reaction mixture was filtered on SiO$_2$ and concentrated. Distillation in a bulb-to-bulb apparatus gave 3.43 g of 12-isobutoxy-4,8-cyclododecadien-1-one.

B.p. 105° C./5.4 Pa; yield 73%.

IR: 1715 cm$^{-1}$.

NMR (60 MHz): 0.91(d,J=7 Hz,6H); 3.15(d,J=7 Hz,2H); 3.7(m,1H); 5.1-5.6(m,4H) δ ppm.

GC-MS (2 peaks, approx. 3:1): (1) 250 (M+,28), 182(9), 133(7), 119(11), 97(12), 79(16), 67(24), 57(89), 41(100). (2) 250 (M+,29), 182(12), 166(7), 120(9), 107(9), 97(12), 79(27), 67(27), 57(100), 41(96).

Odor properties: spicy, aldehydic, calamus/cardamom tonality.

EXAMPLE 4

A base perfuming composition for a masculine "eau de toilette" or an after-shaving lotion was prepared by admixing the following ingredients:

| Ingredients | Parts by weight |
| --- | --- |
| γ-Undecalactone | 200 |
| Carrot essential oil | 300 |
| Cumin essential oil | 300 |
| Estragole | 1200 |
| Clove bud essential oil | 1500 |
| Mandarin essential oil | 3000 |
| Clary sage essential oil | 1800 |
| Synthetic plum | 1200 |
|  | 9500 |

The perfuming base thus prepared can be qualified as being fruity. The addition of 500 parts of 12-pentyloxy-4,8-cyclododecadien-1-one to this composition provided a new composition which developed a more fruity, lactonic and spicy odor. Furthermore, the volume and power of the composition were clearly enhanced. The substitution, in this example, of the above-mentioned perfuming ingredient by 12-isobutoxy-4,8-cyclododecadien-1-one or 12-(2,2-dimethylpropoxy)-4,8-cyclododecadiene, in identical proportions, produced similar effects.

EXAMPLE 5

A base perfuming composition, intended for a powder detergent, was prepared by admixture of the following ingredients:

| Ingerdients | Parts by weight |
| --- | --- |
| Dimethylbenzylcarbinyl acetate | 100 |
| Styralyl acetate | 100 |
| Anisic aldehyde | 19 |
| Hexylcinnamic aldehyde | 2500 |
| Citronellol | 1500 |
| Verdyl acetate | 700 |
| Coumarine | 100 |
| Dihydromyrcenol | 200 |
| p-tert-Butylcyclohexylaldehyde | 500 |
| IRALIA ®[1] | 800 |
| LILIAL ®[2] | 300 |
| MAYOL ®[3] | 200 |
| Phenylethyl alcohol | 1400 |
| TONALID ®[4] | 500 |
| VERTOFIX COEUR ®[5] | 500 |
| | 9500 |

[1] α-methylionone: origin: Firmenich SA, Geneva, Switzerland
[2] α-methyl-p-tert-butylhydrocinnamic aldehyde; origin: L. Givaudan SA, Vernier, Switzerland
[3] 4-isopropylcyclohexylmethanol; origin: Firmenich SA, Geneva, Switzerland
[4] 6-acetyl-1,1,3,4,4,6-hexamethyl-tetrahydronaphthalene; origin: PFW Inc.
[5] origin: IFF Inc.

This perfuming base was a floral-powdery-woody-musky type composition. The admixture of 500 parts by weight of one of the new perfuming ingredients mentioned in the preceding example to this composition provided a new composition which possessed more volume and acquired a functional aldehydic aspect, while developing an orris note.

What we claim is:

1. A method to confer, enhance, improve or modify the odor properties of a perfuming composition or perfumed product, which method comprises adding to said composition or product a fragrance effective amount of a compound of formula

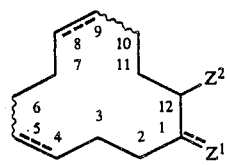

(I)

wherein the symbol $Z^1$ stands for an oxygen atom or an OH group, the dotted lines indicate the location of an endocyclic single or double bond in positions 4 and 8 of the ring and of an exocylic carbon-oxygen single ($Z^1$=OH) or double ($Z^1$=O) bond in position 1, the wavy lines define a C—C bond of E or Z configuration when the bond in positions 4 and 8 is a double bond, and the symbol $Z^2$ stands for a group $OR^3$, wherein $R^3$ represents a linear or branched alkyl radical, containing from 1 to 6 carbon atoms.

2. A perfuming composition comprising as an active ingredient a compound of formula (I) according to claim 1.

3. A perfumed product comprising as an active ingredient a compound of formula (I) according to claim 1.

4. As a product according to claim 3, a perfume or cologne, a soap, a detergent, a household product or a cosmetic preparation.

* * * * *